(12) United States Patent
Harder

(10) Patent No.: US 10,098,766 B2
(45) Date of Patent: Oct. 16, 2018

(54) STENT AND METHOD AND DEVICE FOR FABRICATING THE STENT

(75) Inventor: Claus Harder, Uttenreuth (DE)

(73) Assignee: BIOTRONIK AG, Buelach (CH)

( * ) Notice: Subject to any disclaimer, the term of this patent is extended or adjusted under 35 U.S.C. 154(b) by 2101 days.

(21) Appl. No.: 12/510,166

(22) Filed: Jul. 27, 2009

(65) Prior Publication Data

US 2010/0049300 A1 Feb. 25, 2010

(30) Foreign Application Priority Data

Aug. 19, 2008 (DE) .................. 10 2008 038 367

(51) Int. Cl.
- A61F 2/82 (2013.01)
- A61F 2/915 (2013.01)
- A61F 2/91 (2013.01)
- A61F 2/06 (2013.01)

(52) U.S. Cl.
CPC ................ *A61F 2/915* (2013.01); *A61F 2/82* (2013.01); *A61F 2/91* (2013.01); *A61F 2002/068* (2013.01); *A61F 2002/9155* (2013.01)

(58) Field of Classification Search
CPC .... A61F 2/82; A61F 2/91; A61F 2/915; A61F 2230/0008; A61F 2230/0017; A61F 2230/0013; A61F 2230/0034; A61F 2002/068; A61F 2002/30187

See application file for complete search history.

(56) References Cited

U.S. PATENT DOCUMENTS

| | | | |
|---|---|---|---|
| 5,718,713 A * | 2/1998 | Frantzen | ...... 623/1.15 |
| 6,685,737 B1 | 2/2004 | Pacetti | |
| 2008/0082162 A1 | 4/2008 | Boismier et al. | |
| 2008/0142050 A1 | 6/2008 | Hashish et al. | |
| 2009/0204203 A1* | 8/2009 | Allen | ...... A61F 2/915 623/1.34 |
| 2011/0276123 A1* | 11/2011 | Davies | ...... A61F 2/88 623/1.15 |

FOREIGN PATENT DOCUMENTS

| | | |
|---|---|---|
| DE | 199 16 086 A1 | 10/1999 |
| DE | 601 23 567 T2 | 6/2007 |
| WO | WO 98/55048 | 12/1998 |
| WO | WO 02/47581 A1 | 6/2002 |
| WO | WO 2006/086069 A3 | 8/2006 |

OTHER PUBLICATIONS

Search report for priority application DE 10 2008 038 367.8; Germany.
EP Search Report for EP 09 16 6091.

* cited by examiner

*Primary Examiner* — Dinah Baria

(74) *Attorney, Agent, or Firm* — Wagenknecht IP Law Group PC

(57) ABSTRACT

Stent, as well as a method and device for fabricating the stent, wherein the stent has a tubular lattice structure comprising individual struts and at least one strut of which at least one longitudinal section runs with at least one directional component in the radial circumferential direction of the stent, wherein the surface of the longitudinal section facing the outside of the stent is curved only about the longitudinal axis of the stent. According to the invention, the surface of longitudinal section of the strut, which surface faces the inside of the stent, has such a curvature that the strut cross section is fluidically optimized.

9 Claims, 3 Drawing Sheets

STENT AND METHOD AND DEVICE FOR FABRICATING THE STENT

CROSS-REFERENCE TO RELATED APPLICATIONS

This application claims benefit of priority to German patent application number DE 10 2008 038 367.8, filed on Aug. 19, 2008; the contents of which are herein incorporated by reference in their entirety.

FIELD OF THE INVENTION

This invention relates to a stent that comprises struts, a method of fabricating the stent, as well as a device for implementing the method.

BACKGROUND OF THE INVENTION

Stents are typically endovascular prostheses that are used for the therapy applied to stenoses. They essentially comprise a support structure by which the wall of a vessel, such as, for example, an artery, is braced so as to ensure sufficient flow through the vessel. In addition, an aneurysm can be bridged by the stent. During implantation, the stent is inserted in a compressed state into the vessel and then expanded at the site to be treated. Expansion of the stent is typically effected by means of a balloon catheter that has been previously inserted into the interior of the stent and also functions to position the stent within the vessel. As a result of the expansion of the stent, the walls of the support structure are pressed against the vascular wall, thereby effecting an adequate sectional area of flow for the vessel. In order to ensure that the sectional area of flow is not reduced too much by the stent itself, stents generally have very narrow wall thicknesses in the region of the support structure. These narrow wall thicknesses must, however, ensure that the expanded shape of the stent is preserved despite a pressure applied by the vessel and acting radially on the stent. In addition to radial strength, the requirement also to be met by the stent is to have sufficient flexural stiffness to enable the stent to adapt as well as possible to the partially bent shape and the movements of the vascular section in which it is implanted.

Typically, the support structure of the stent here is essentially lattice-shaped, although this lattice can have a wide variety of designs. The lattice structure is typically generated by a laser cutting process targeted at a lateral cylindrical surface of a tube.

The struts forming the lattice structure thus have an essentially rectangular cross section, as shown in FIG. 2 which illustrates the prior art. The disadvantageous aspect of the embodiment of the strut 200 shown in FIG. 2 is that the blood flow 211 passing over strut 200 tends to form turbulences 213, with the result that a turbulent flow is created in the region of strut 200 instead of the desired laminar flow. Turbulences 213 result in unwanted deposits along with the possible consequential effects of neointimal hyperplasia and arthrosclerosis 212. These deposits can develop further into a symptomatic restenosis. This effect is found particularly in the case of proximally-located struts and decreases in the distal direction.

Various measures are known involving treating the struts after the laser-cutting procedure. The struts are treated, for example, by electropolishing. The rounding of edges produced thereby is so small, however, that it does not produce any significant change in the flow from turbulent into laminar. In addition, electropolishing is used to treat the entire support structure, with the result that it is not possible to perform a selective treatment of the proximal end of the stent. Furthermore, the slight removal of material here essentially is effected symmetrically over the strut, that is, on the mural edges, the edges facing the vascular wall, and on the luminal edges facing the vascular lumen—all of which does not counteract the formation of turbulences.

An ellipsoid cross-sectional surface for the strut is known from EP 0 824 903 A1 which differs from the cross section of a strut as described and illustrated in FIG. 2. A cross-sectional shape is shown in FIG. 2 of this publication in which both the luminal as well as the mural surfaces are curved around the longitudinal axis of the strut. It is the curvature of the mural surface in particular that is disadvantageous in that a strut curved in this way penetrates more deeply into the vascular wall during dilatation, thereby damaging this wall to a greater extent. The result is an increase in neointimal proliferation which in turn promotes the formation of deposits. The luminal surface of the strut is curved symmetrically. It is well known that symmetrical curvatures have an adverse effect on fluid flows in so far as they are unable to produce a laminar flow. This means that turbulences of the blood flow passing over the luminal surface occur even in this ellipsoid embodiment shown in EP 0 824 903 A1, which turbulences in turn also result in the formation of deposits. Another disadvantage of the strut cross sections referenced in this document is the reduction in its axial section modulus which in particular has a disadvantageous effect on the strength of the stent in response to increased bending stress. In addition, the radial strength of the stent is lowered by the decreased wall thickness of the support structure.

Particularly in the case of novel stents composed of magnesium alloys, relatively large wall thicknesses are required for reasons of strength, with the result that the cross-sectional shapes of the struts disclosed in EP 0 824 903 A1 are not usable for such stents without unduly reducing the radial strength of the stent. In order to fabricate stents from magnesium alloys that have the requisite radial strength and using these types of web cross sections as known in the referenced prior art, the struts would have to have significantly larger dimensions in cross section. This is disadvantageous, however, because the sectional area of flow of the blood vessel is reduced thereby, which effect results in turbulences and increased formation of deposits.

US 2008/0082162 A1 discloses various strut cross sections, although these have a coating on their mural surface. Curvatures of luminal strut surfaces are of symmetrical form, as a result of which once again the referenced unwanted deposits appear on the strut when inserted in the blood stream.

The fundamental problem to be solved by this invention is to provide a stent, as well as a method of fabricating the stent, wherein the objective is to design the stent such that vascular constriction is minimized while at the same time sufficient flexural and radial stiffness of the stent is provided.

SUMMARY OF THE INVENTION

According to the invention, a stent is provided that has a tubular, individual-struts-comprising lattice structure, wherein the stent has at least one strut, of which at least one longitudinal section runs with at least one directional component in the radial circumferential direction of the stent, and wherein the radially outward-facing (mural) surface of the longitudinal section of the strut is curved only around one longitudinal axis of the stent. According to the invention, the surface of the strut's longitudinal section (luminal) facing towards the inside of the stent has a curvature such that the cross section of the strut is fluidically optimized. The invention thus relates to the design of a strut, or also only of a longitudinal section of a strut, that runs with at least one directional component in a radial circumferential direction of the stent. This means that the strut, or its longitudinal section, runs parallel to a tangent applied to the circumference of the stent, or has one component that is oriented in this direction. What is excluded according to the invention, however, are the longitudinal strut sections that run only parallel to the longitudinal axis of the stent. This fundamentally distinguishes the stent according to the invention from the embodiments shown in EP 0 824 903 A1. These types of struts according to the invention can be easily cut from a tube by laser. What is understood by the strut cross section is that cross section which is produced by a section in the longitudinal axis of the stent through the longitudinal section of the strut with one directional component in the radial circumferential direction, in other words, performed in the direction of the longitudinal axis of the stent. According to the invention, the strut in cross section has only on the luminal surface in its longitudinal direction a curvature which is designed to prevent turbulences of the blood flow passing through the stent, and thus prevent deposits. On the mural side, the strut has no curvature in the cross section running in the longitudinal direction of the stent. This design is particularly advantageous since the mural contact surface of the strut on the vascular wall is not thereby reduced, and thus the pressure of the strut on the vascular wall is limited, thereby reducing the risk of damage to the vessel.

In order to effect the optimal prevention of turbulences, the stent according to the invention should be designed such that the luminal surface of the strut has an optimally curved surface. The optimal curvature is found by the person skilled in the art based on tests or conventional flow simulation models and can be, among other factors, a function of the sectional area of flow of the vessel and of the flow velocity.

In a preferred embodiment of the stent according to the invention, provision is made whereby the stent's inward-facing curvature of the strut's surface is designed to be asymmetrically convex. This means that as viewed in cross section the curvature of the luminal surface can have at every point a different distance from the mural surface of the strut section, where the convex curvature is of asymmetric shape. In other words, the curvature of the luminal surface, as viewed in cross section, has different convex regions that determine the asymmetry. The asymmetry in the convex shape produces a streamlined design of the strut cross section, as a result of which the blood flow passing through the stent flows laminarly in the region of the strut and deposits on the strut are prevented. It is specifically this laminar flow motion of the blood effected by the cross section that has the additional very important effect of promoting the endothelialization of the stent, which is the "in-growth" with the endothelial cells. This too results in the prevention of deposits.

Provision can be made here whereby the stent according to the invention comprises biodegradable material in the region of the strut. In another embodiment, provision can be made whereby the strut is composed entirely of biodegradable material. Those materials are defined as biodegradable within the meaning of the invention in which a decomposition takes place within a physiological environment, this decomposition ultimately resulting in a condition whereby the entire implant, or the part of the implant composed of this material, looses its mechanical integrity.

Preferably, this biodegradable material is a biodegradable metal, preferably, a biodegradable alloy selected form the group magnesium, iron, and tungsten; in particular, the biodegradable material is a magnesium alloy. What is understood by alloy here is a metallic microstructure, the principal components of which are magnesium, iron, or tungsten. The main component is the alloy component in which the weight percentage of the alloy is the highest. A percentage for the main component is preferably 50 wt. %, in particular, more than 70 wt. %.

If the material is a magnesium alloy, this preferably contains yttrium and other rare-earth metals since such an alloy excels in terms of its physiochemical properties and high bio-compatibility, also in particular in terms of its products of decomposition.

What is especially preferred for use is a magnesium alloy with the composition of rare-earth metals being 5.2-9.9 wt. %, of which yttrium is 0.0-5.5 wt. % and the remainder is <1 wt. %, where magnesium makes up the missing fraction of the alloy up to 100 wt. %. Both experimentally and in initial clinical trials, this magnesium alloy has confirmed its special applicability, i.e., demonstrates high biocompatibility, advantageous working properties, good mechanical characteristics, and a degradation behavior that is suitable for the intended applications. The collective term "rare-earth metals" primarily denotes scandium (21), yttrium (39), lanthanum (57), and the following elements following lanthanum (57), specifically, cerium (58), praseodymium (59), neodymium (60), promethium (61), samarium (62), europium (63), gadolinium (64), terbium (65), dysprosium (66), holmium (67), erbium (68), thulium (69), ytterbium (70) und lutetium (71). The alloys of the elements magnesium, iron, and tungsten must thus be selected in terms of their composition so as to be biodegradable.

Alternatively, what can be employed in place of a material based on metal is a biodegradable polymer. Preferred polymers for the polymer matrix of the implant according to the invention are selected from the group polydioxanone, polyglycolide polycaprolactone, polylactide (poly-l-lactide, poly-d,l-lactide, and copolymers and blends such as poly(l-lactide-co-glycolide), poly(d,l-lactide-co-glycolide), poly(l-lactide-co-d,l-lactide), poly(l-lactide-co-trimethylene carbonate, triblock copolymers), polysaccharides (chitosan, levan, hyaluronic acid, heparin, dextran, cellulose, etc.), polyhydroxyvalerate, ethylvinylacetate, polyethylene oxide, polyphosphorylcholin, fibrin, albumin.

Alternatively, provision can be made whereby the strut is composed of a permanent material that does not decompose. The base body of the permanent stent is preferably composed of a metal material consisting of one or more metals from the group iron, nickel, tungsten, zirconium, niobium, tantalum, zinc, or silicon, and optionally, a second component consisting of one or more metals from the group lithium, sodium, potassium, calcium, manganese iron, or tungsten, preferably consisting of a zinc-potassium alloy. In another exemplary embodiment, the base body is composed of a shape-memory material consisting of one or more materials from the group composed of nickel-titanium alloys and copper-zinc-aluminum alloys, preferably, however, of Nitinol. In another preferred embodiment, the base body of the stent is composed of stainless steel, preferably consisting of a Cr—Ni—Fe steel—here preferably the alloy 316L—or a Co—Cr steel. In addition, the base body of the stent can be composed at least in part of a plastic and/or a ceramic.

In a first alternative embodiment of the invention, provision is made whereby all of the strut sections of the stent that run with one directional component perpendicular to the longitudinal direction of the stent are designed in accordance with the present invention. As a result, the embodiment of the strut according to the invention is not restricted to specific sections of the stent; instead, all struts of those stents in general can be designed according to the invention which has a directional component perpendicular to the longitudinal direction of the stent. In a second alternative embodiment, the stent has struts that are designed according to the invention only at its end regions, where the end regions, starting from one stent end each, each extend over 20 to 30 percent of the length of the stent. This means that the struts are designed in a fluidically optimized fashion only at the end regions of the stent. The center region of the stent—aside from the conventional electropolishing, which continues to be employed, used to smooth the strut surfaces and to preclude sharp strut edges—thus does not undergo any surface treatment of the strut that significantly modifies the strut cross section. This may be sufficient for simple stents since experience shows that the deposits occur only at the end regions of the sent (usually at the proximal end of the stent) and not at the center of the stent. This embodiment has the advantage that the wall thickness of the stent, that is, the material thickness of the strut in the center region of the stent, is of thicker design than at least at the proximal stent end. It is also possible to implement the stent such that a surface treatment of varying degree is performed over the length of the stent, thereby making the cross-sectional area of the strut larger as the strut becomes more centrally located in the stent. This means that the removal of material so as to effect the fluidic optimization of the strut cross section becomes greater the further away a strut is located at the end of the stent. This in turn has the advantage that the wall thickness is made thickest specifically in that region of the stent in which the greatest bending stress is found when a bending moment is applied to the stent end. As a result, the stent ends here remain flexible and can thus more easily adapt to movements of tissue. Another advantage is that the transition between region in which the vascular wall is supported by a stent of this design and the vascular wall immediately adjacent to the stent ends is "soft." This means that the elasticity of the vessel increases or decreases non-incrementally. In other words, an abrupt drop in elasticity between unsupported tissue wall and vascular wall is prevented. This minimizes mechanical irritation at the stent ends and in turn lowers the risk of focal stenoses at the stent ends.

In a preferred embodiment of the invention, provision is made whereby the stent according to the invention is constructed mirror-symmetrically. This means that, for example, convex asymmetries are arranged and shaped along the surface curvatures of the luminal strut surfaces such that they have a different, in each case opposite, orientation on each half of the stent. The mirror plane here runs perpendicular to the stents longitudinal axis precisely at the longitudinal center of the stent. Although based on this design one end of the stent is not in fact of optimal fluidic shape due to its asymmetry and position within the vessel when inserted in the blood stream, this disadvantage is nevertheless acceptable since this stent region constitutes the end for the stent at which only minimal deposits occur due to very small turbulences. The proximal end of the stent, however, is optimized in any case, with the result that deposits are prevented according to the invention at this end. This design has the advantage that implantation of the stent is orientation-independent since each of the ends of the stent is fluidically optimized and can thus form the proximal end of the stent independently of the orientation of the stent when in use.

In an alternative design, provision can be made whereby the asymmetries of the curvatures on the struts are oriented unilaterally over the entire length of the stent. As a result, mirror symmetry of the stent no longer exists, while on the other hand the advantage is created whereby both ends of the stent are of optimal fluidic design and thus any possible minimally occurring deposits at the distal end can be prevented. However, care must be taken during implantation with this design so as to ensure that the proximal end of the stent is the optimized end in terms of the direction of flow.

Strut cross sections designed according to the invention can have a thickness of between 60 to 185 μm, preferably, of between 60 and 90 μm. That means that the wall thickness of the supporting structure of the stent according to the invention also lies within these indicated micrometer ranges.

Another aspect of the present invention is the use of the stent according to the invention as an implant in a vessel to prevent vascular construction. The stent according to the invention thus relates to an embodiment that is fabricated such that it already has the fluidically-optimized curved surface on the luminal side of the strut during implantation. This distinguishes the stent according to the invention from embodiments in which a strut cross section that is at least partially adapted to the blood flow does not result until after relatively long implantation of the stent due to material erosion of the strut. By using the stent according to the invention, it is thus possible to prevent deposits immediately after implantation.

A method is also provided according to the invention for producing the stent according to the invention wherein the lattice structure of the stent is produced such that at least one longitudinal section of the strut running with at least one directional component in the radial circumferential direction of the stent has an essentially angular cross section, wherein a rounding is effected of the luminal edges, and edges of the longitudinal section of the strut running with at least one directional component in the radial circumferential direction of the stent, said round being effected by at least one particle beam directed at the edges.

The lattice structure is generated in the conventional fashion by laser cutting of the tube. The particles of the particle beam here can comprise fine-grained sand or spherical pellets composed of a solid material. Due to scattering of the particle beam, the beam also strikes edges that are not located directly within the projection range of a nozzle from which the particle beam emerges. The slight tumbling motion or gyrating motion of the particle beam ensures that the particles strike to a sufficient degree all strut edges located in front of the nozzle within the range of the beam. This thus enables a rounding to be produced of the luminal edges of the strut such that these edges have the fluidically optimized cross section according to the invention.

Provision is made advantageously here whereby the two luminal edges of the longitudinal section of the strut are each worked by one particle beam, where the directions of the two particle beams are opposed to each other.

The method is advantageously designed if the particle beam from one nozzle inserted into the stent is oriented towards the edge of the strut pointing towards the nozzle, and the nozzle withdrawn from the stent so as to effect sequential irradiation of multiple struts disposed side by side in the longitudinal direction of the stent. A scattering of the particle beam is effected here such that all of the strut edges lying within one section perpendicular to the longitudinal direction of the stent are irradiated simultaneously.

The irradiation of the edges here is effected bilaterally, where the nozzle is drawn at least once from the stent towards the first stent end and at least once from the stent towards the second stent end. The nozzle here does not have to be inserted completely into the stent; instead, what is sufficient for treating the stent end regions is to insert the nozzle only into this end region and to withdraw it from the stent as the particle beam is applied. Alternatively, the nozzle is inserted completely into the stent and drawn from the end opposite the insertion end only through this opposing end region while applying the particle beam, thereby irradiating this end region from the other side.

Both variants of the method should be employed to effect rounding of the two luminal edges of the longitudinal section of the strut. It is possible here to perform both variants with different particle densities, different volumetric flow rates, different speeds for withdrawal of the nozzle, and/or a different number of irradiation operations so as to create the asymmetrically convex curvature of the luminal surfaces of the strut.

In order to effect the final treatment of the stent, provision is made whereby the stent is treated by electropolishing after particle-beam irradiation. The electropolishing here functions to effect the rounding of the edges such that aside from luminal the edges the mural edges of the strut are also somewhat rounded so as to preclude any cutting into the vascular wall. Despite the rounding of the mural edges, the mural surface of the strut is nevertheless not modified comprehensively in such a way that an overall curvature of the surface would result. Electropolishing also functions to effect the final surface smoothing of the entire support structure of the stent.

Provision is advantageously made whereby the speed of withdrawing the nozzle is varied. This means that, for example, when the nozzle is withdrawn from one end region of the stent it is first withdrawn more quickly and then more slowly, thereby effecting a removal of less material at the side of the end region facing the center of the stent than at the stent end.

According to the invention, a device is also provided to implement the method according to the invention, wherein this device comprises a reservoir to supply beam particles, an appliance to generate high pressure, a conduit to transport the particle beam, and a nozzle connected to the transport conduit, wherein at least the nozzle has such geometrical dimensions so as to make it insertable into a stent. The reservoir can, for example, be a tank inside of which there is high pressure. A conventional pump can be used to generate the high pressure. The transport conduit can be a tube or a pipe to which a nozzle is connected. The transport conduit here can be designed such that the nozzle is created by an open end of the transport conduit as long as this end is capable of being inserted into a stent and generating a particle beam. In this case, the nozzle is an integral component of the transport conduit.

The stent according to the invention can thus be rounded at its luminal edges by means of the method according to the invention and associated device such that the blood flow passes laminarly along the struts designed according to the invention. The mural edges here are not rounded beyond what is achievable by standard electropolishing so as to keep the mural support surface as large as possible and thereby minimize the pressure on the vascular wall in order to prevent injury. The asymmetrical cross-sectional shape of the strut is fluidically optimized, wherein this can be designed according to fluidic simulation models. For example, an asymmetrical rounding of the luminal edges can be effected at the stent end regions, wherein in particular the proximal end of the stent is fluidically optimized. As a result, the formation of deposits along the strut is prevented and the risk of unwanted neointimal hyperlasias and arteriosclerotic phenomena is reduced. Due to the fact that the removal of material occurs preferentially at the stent end regions, the wall thickness of the support structure is reduced only in these stent end regions. This means that the center region of the stent has a wall thickness of the support structure that matches the wall thickness of the tube from which the support structure has been cut out. The result is a reduced flexural stiffness at the stent ends and a by comparison increased flexural stiffness at the stent center. These properties are advantageous in particular in the event the stent when in use must follow motions of the vessel in which it has been inserted. This means that the stent designed according to the invention can more easily participate in the motion of the vessel, thereby avoiding breaks or gaps between the stent end and the vascular wall resting thereon, with the result that the risk of deposits' forming in this region is reduced.

BRIEF DESCRIPTION OF THE DRAWINGS

The invention is described below based on the attached drawings. In the drawings.

DETAILED DESCRIPTION OF PREFERRED EMBODIMENTS

Figure 1:
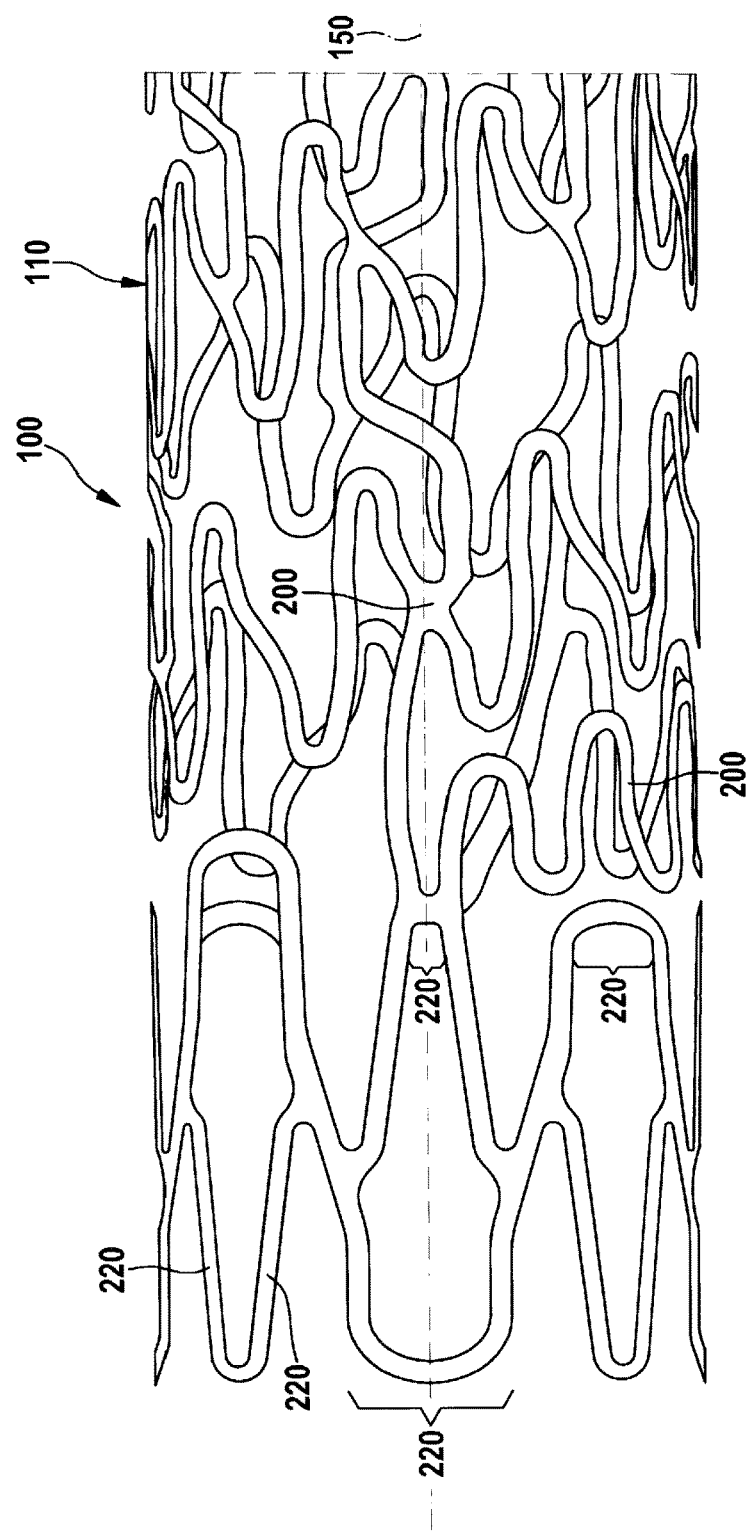
FIG. 1 illustrates a section of a possible support structure of a stent according to the invention.
Figure 2:
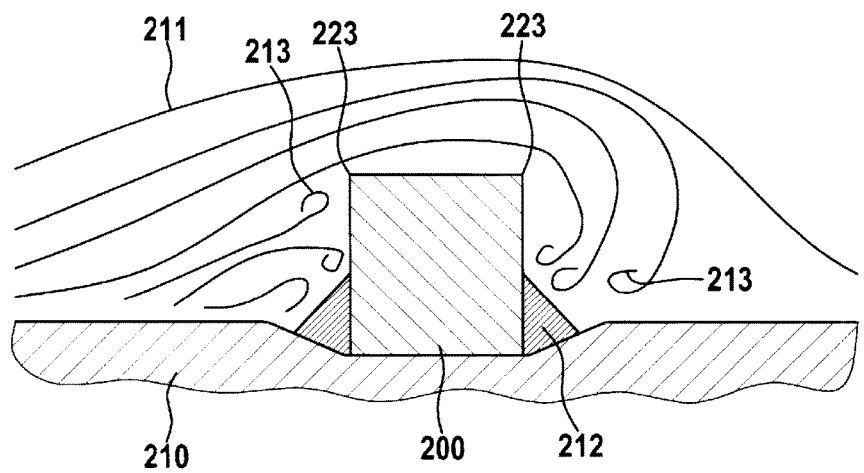
FIG. 2 illustrates a cross section of a conventional strut in use running perpendicular to the longitudinal direction of the stent.

FIGS. 1 and 2 illustrate struts 200 such as those conventionally used in the support structure or lattice structure 110 of a stent 100. The invention here is not restricted to the design of the lattice structure 110 illustrated in FIG. 1; instead, the invention can comprise all stent structures that have struts and in which the longitudinal sections have at least one directional component that runs in the radial circumferential direction of the stent. This refers to those longitudinal sections 220 that, as shown in FIG. 1, do not run parallel to the longitudinal axis 150 of stent 100. This thus refers to longitudinal sections 220 that obviously run in a radial circumferential direction but also to the longitudinal sections that run obliquely relative to the longitudinal axis since these longitudinal sections have also a directional component that runs perpendicular to the longitudinal axis.

It is thus evident in FIG. 2 that the surfaces of the strut facing the outside of the stent, that is, the mural surfaces that that contact the vascular wall 210, do not have any curvature in the cross section shown. This means that these surfaces are curved only in one direction, specifically, about longitudinal axis 150. In the stent according to the invention, curvature of the mural strut surfaces is not affected about axes that are perpendicular to longitudinal axis 150.

Figure 3:
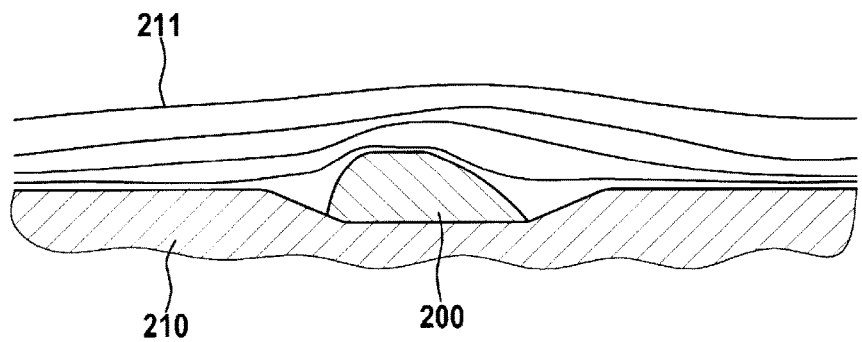
FIG. 3 illustrates the cross section of a strut designed according to the invention and running perpendicular to the longitudinal direction of the stent.

The invention is made clear in particular by a comparison of the cross-sectional shape of the strut in FIG. 3 and the conventional cross-sectional shape in FIG. 2. Because of the luminal edges 223 on conventional strut 200, as shown in FIG. 2, a turbulence 213 of the blood stream 211 is created that results in the formation of deposits 212 between vascular wall 210 and strut 200. These deposits can have arteriosclerotic effects and must be reduced or prevented.

The cross section of strut 200 is optimized by the design of strut 200 according to the invention, as shown in FIG. 3, whereby a laminar blood flow 211 is formed. Deposits are thereby prevented.

It is evident in FIG. 3 that the cross section of strut 200 is designed to be asymmetrically convex. Formation of the laminar flow is promoted in particular by the asymmetry.

Figure 4:
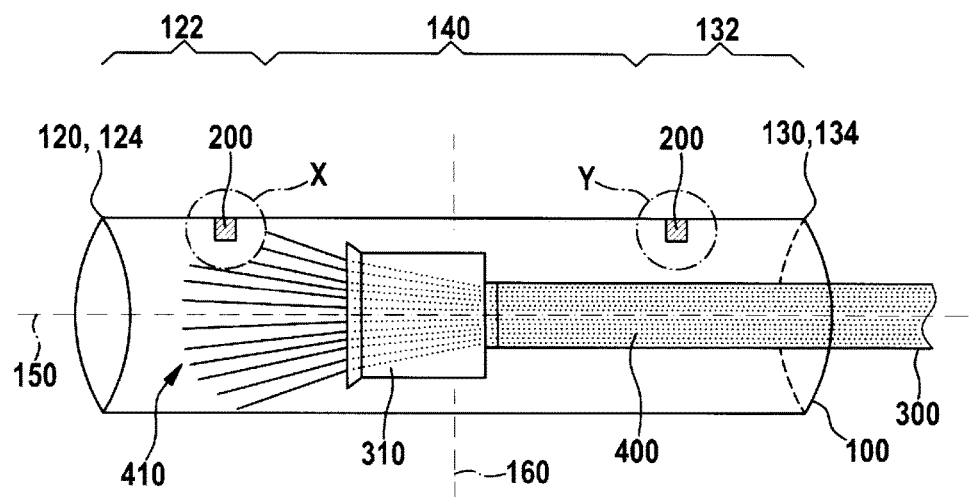
FIG. 4 illustrates a schematically drawn stent comprising a nozzle inserted therein and particle beam.

FIG. 4 illustrates the way in which the fluidically optimized rounding of the struts can be produced. A schematically illustrated stent 100 is shown that is formed from a plurality of struts 200 similar or identical to the design shown in FIG. 1. For reasons of clarity, only one stent 200 is shown in cross section on each side of the stent, which cross section is also shown in enlarged views in FIG. 5.

To implement the method according to the invention, a transport conduit 300 is inserted into stent 100 at the end of which a nozzle 310 is disposed. Transport conduit 300 conveys particles 400 to nozzle 310 from which particles 400 exit as a particle beam 410. Particle beam 410 exhibits a certain scattering, with the result that particles 400 exiting nozzle 310 laterally strike struts 200 and also the luminal surface of longitudinal section 221 of strut 200. What is achieved by impinging particles 400 is that luminal edges 223 are rounded. Nozzle 310 is withdrawn from stent 100 in the direction of second stent end 130. Alternatively, the nozzle can also be pushed through stent 100 towards the first stent end 120, although here care must be taken that no obstruction in the displacement of nozzle 310 is effected by residual particles 400 remaining in stent 100 due to the irradiation procedure.

Figure 5:
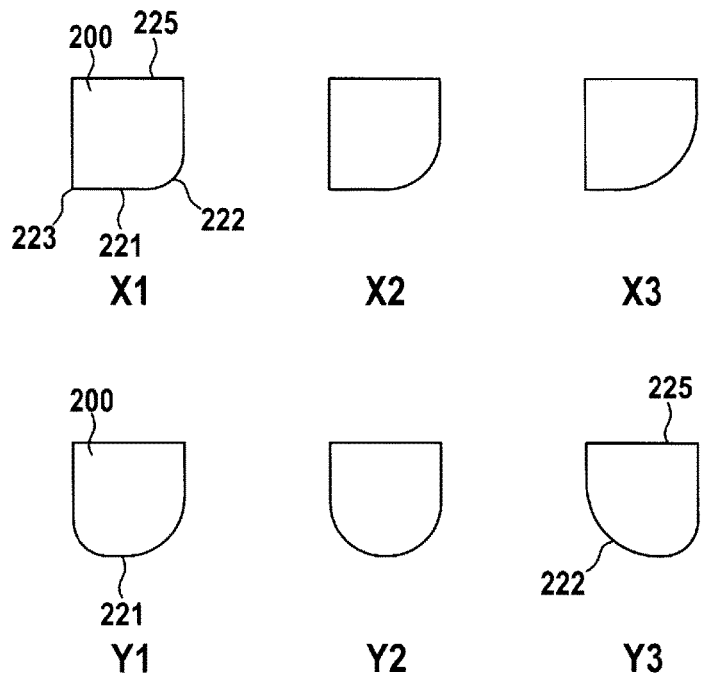
FIG. 5 is a schematic view showing individual treatment stages of the strut.

As a result of repeated or sustained irradiation of strut 200, as is illustrated in FIG. 5 in the separate diagrams showing an enlargement of region X from FIG. 4, it is evident that a luminal edge 223 of strut 200 is being rounded. What results is a curvature 222, the radius of which becomes increasingly greater the longer, or more frequently, the beam is directed at strut 200.

Separate diagrams Y1 through Y3 in FIG. 5 shows strut 200 in an enlarged view of the region in FIG. 4 identified by Y. It is evident that in strut 200 shown here rounding has already taken place on the two luminal edges 223, with the result that a curvature 222 has already formed on the luminal surface of longitudinal section 221, which curvature, as is especially evident in FIG. 5, is of asymmetrically convex shape. In order to achieve this cross-sectional shape of the strut shown by Y3 in FIG. 5, nozzle 310 is first withdrawn, as shown in FIG. 4, from first stent end 120 towards second stent end 130, then removed from stent 100. This operation can be repeated. What results thereby is the cross-sectional shapes indicated in diagrams X1 through X3.

To effect the rounding of the still-present luminal edge 223, nozzle 310 is drawn in a manner analogous to that described for second stent end 130 towards first stent end 120, then withdrawn from the stent. What results is, as shown in the cross-sectional shape illustrated for Y3 in FIG. 5, an additional removal of material in response to prolonged or repeated irradiation, this removal resulting in the asymmetrically convex shape of the cross section.

The invention is not, however, restricted to this procedure; instead provision can be made whereby nozzle 310 is drawn only from stent center 140 respectively towards first stent end 120 and second stent end 130, thereby rounding corresponding luminal edges 223. Preferably, provision can be made whereby only those struts 200 are rounded which are disposed at the two end regions 122 and 132, with the result that struts 200 located at stent center 140 are not rounded by particle beam 410.

In addition, provision can be made whereby stent 100 is of mirror-symmetrical design such that its two halves are of symmetrical design along mirror-symmetrical axis 160. In this case, the struts 200 shown in regions X and Y in FIG. 4 are fabricated such that their convex curvatures have different and opposing orientations. This type of design has the advantage that the stent according to the invention can be implanted in the vessel in an orientation-independent manner since its proximal end 134 is in any case of fluidically optimized design. The somewhat less advantageous design of distal end 124 in this case does not have any disruptive effect since no deposits, or only minimal deposits, are to be expected at the distal end.

Alternatively, the stent can be designed such that all asymmetrically convex curvatures have the same orientation. This means that all strut cross sections can have, for example, the shape illustrated in Y3 of FIG. 5. This design has the advantage of the fluidically optimized shape of all struts 200, although care must still be taken during implantation of the stent that stent 100 is implanted in the vessel such that the end optimized in terms of the direction of flow is proximal end 134 of stent 100.

It is evident in the diagrams of FIG. 5 that the mural surface of longitudinal section 225 is not rounded by the particle beam.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

LIST OF REFERENCE NOTATIONS stent 100
lattice structure 110
first stent end 120
first end region 122
distal end 124
second stent end 130
second end region 132
proximal end 134
stent center 140
longitudinal axis 150
mirror-symmetrical axis 160
strut 200
vascular wall 210
blood flow 211
deposit 212
turbulence 213
longitudinal section 220
surface of the luminal longitudinal section 221
curvature 222
luminal edge 223
mural surface of the longitudinal section 225
transport conduit 300
nozzle 310 particle 400
particle beam 410

What is claimed is:

1. A stent, comprising a tube-like lattice structure comprising individual struts, wherein the stent has at least one strut, positioned at a first end region of the stent, and at least one strut, positioned at a second end region of the stent opposing the first end region, wherein each of the at least one strut at the first and second end regions have at least one longitudinal section that does not run parallel to a longitudinal axis of the stent, wherein the inner surface of each of the at least one strut at the first and second end regions is of an asymmetric convex shape defined by a plane of asymmetry perpendicular to the longitudinal axis of the stent and longitudinally aligned at a middle of the at least one strut, and wherein the asymmetric convex shape of the at least one strut at the first end region is a mirror image of the asymmetric convex shape of the at least one strut at the second end region, defined by a plane of mirror symmetry perpendicular to the longitudinal axis of the stent.

2. The stent according to claim 1, wherein the stent comprises a biodegradable material.

3. The stent according to claim 1, wherein all of the struts of the stent have at least one longitudinal section that does not run parallel to the longitudinal axis of the stent.

4. The stent according to claim 1, wherein the at least one strut at the first end region is separated from the at least one strut at the second end region by at least one innermost strut having an inner surface lacking a rounded shape, wherein each of the first and second end regions extends over 20-30% of the length of the stent, starting from each stent end.

5. The stent according to claim 1, wherein the at least one strut at the first end region is separated from the at least one strut at the second end region by an innermost strut comprising a greater thickness than each of the at least one strut of the first and second end regions.

6. A stent, comprising a tube-like lattice structure comprising individual struts, wherein the stent has at least one strut, positioned at a first end region of the stent, and at least one strut, positioned at a second end region of the stent opposing the first end region, wherein each of the at least one strut at the first and second end regions have at least one longitudinal section that does not run parallel to a longitudinal axis of the stent, wherein the outside surface of each of the at least one strut at the first and second end regions is curved about the longitudinal axis of the stent, and wherein the inner surface of each of the at least one strut at the first and second end regions is of an asymmetric convex shape defined by a plane of asymmetry perpendicular to the longitudinal axis of the stent and longitudinally aligned at a middle of the at least one strut, further wherein the asymmetric convex shape of the at least one strut at the first end region is a mirror image of the asymmetric convex shape of the at least one strut at the second end region, defined by a plane of mirror symmetry perpendicular to the longitudinal axis of the stent, thereby providing the stent with a fluidically optimized proximal end that is independent of implantation orientation.

7. The stent according to claim 6, wherein the stent comprises a biodegradable material.

8. The stent according to claim 6, wherein the at least one strut at the first end region is separated from the at least one strut at the second end region by at least one innermost strut having an inner surface lacking a rounded shape, wherein each of the first and second end regions extends over 20-30% of the length of the stent, starting from each stent end.

9. The stent according to claim 6, wherein the at least one strut at the first end region is separated from the at least one strut at the second end region by an innermost strut comprising a greater thickness than each of the at least one strut of the first and second end regions.

\* \* \* \* \*